United States Patent
Ryu et al.

(10) Patent No.: US 11,787,706 B2
(45) Date of Patent: Oct. 17, 2023

(54) FILTER ASSEMBLY FOR DISINFECTING PATHOGENS USING MULTIPLE WAVELENGTH ULTRAVIOLET LIGHT EMITTING DIODES (UV-LEDS) AND METHOD THEREFOR

(71) Applicant: U.S. Environmental Protection Agency, Washington, DC (US)

(72) Inventors: Hodon Ryu, Cincinnati, OH (US); Hyoungmin Woo, Cincinnati, OH (US)

(73) Assignee: U.S. Environmental Protection Agency, Washington, DC (US)

(*) Notice: Subject to any disclaimer, the term of this patent is extended or adjusted under 35 U.S.C. 154(b) by 142 days.

(21) Appl. No.: 17/386,228

(22) Filed: Jul. 27, 2021

(65) Prior Publication Data

US 2021/0371304 A1 Dec. 2, 2021

Related U.S. Application Data

(62) Division of application No. 16/520,880, filed on Jul. 24, 2019, now Pat. No. 11,104,591.

(51) Int. Cl.
| | | |
|---|---|---|
| C02F 1/32 | (2023.01) | |
| C02F 1/72 | (2023.01) | |
| A61L 2/26 | (2006.01) | |
| A61L 2/10 | (2006.01) | |
| A61L 2/08 | (2006.01) | |

(52) U.S. Cl.
CPC .............. *C02F 1/325* (2013.01); *A61L 2/088* (2013.01); *A61L 2/10* (2013.01); *A61L 2/26* (2013.01); *C02F 1/725* (2013.01); *A61L 2202/11* (2013.01); *A61L 2202/122* (2013.01); *C02F 2201/3222* (2013.01); *C02F 2201/3227* (2013.01); *C02F 2201/3228* (2013.01); *C02F 2303/04* (2013.01); *C02F 2305/10* (2013.01)

(58) Field of Classification Search
CPC .. C02F 1/325; C02F 1/725; C02F 2201/3222; C02F 2201/3227; C02F 2201/3228; C02F 2303/04; C02F 2305/10; C02F 2201/3221; C02F 2307/06; A61L 2/088; A61L 2/10; A61L 2/26; A61L 2202/11; A61L 2202/122; E03C 1/06; E03C 1/04; E03C 1/0409; E03C 2201/40; B05B 15/62; B05B 1/18
See application file for complete search history.

(56) References Cited

U.S. PATENT DOCUMENTS

| | | | |
|---|---|---|---|
| 10,099,944 B2* | 10/2018 | Smetona | A61L 2/10 |
| 10,968,115 B2* | 4/2021 | Hoehne | E03C 1/06 |
| 2015/0114912 A1* | 4/2015 | Taghipour | C02F 1/325 |
| | | | 210/748.14 |
| 2019/0049129 A1* | 2/2019 | Huang | A61L 9/205 |

* cited by examiner

*Primary Examiner* — Xiuyu Tai
(74) *Attorney, Agent, or Firm* — Weiss & Moy, PC; Jeffrey D. Moy

(57) ABSTRACT

A point-of-use (POU) water filtration device has a container. A plurality of channels is formed within the container, water entering the container flowing through the plurality of channels. A plurality of Ultraviolet (UV) Light Emitting Diodes (LEDs) is provided. Each of the plurality of UV LEDs illuminating UV light down an associated channel of the plurality of channels.

16 Claims, 4 Drawing Sheets

FILTER ASSEMBLY FOR DISINFECTING PATHOGENS USING MULTIPLE WAVELENGTH ULTRAVIOLET LIGHT EMITTING DIODES (UV-LEDS) AND METHOD THEREFOR

RELATED APPLICATIONS

This patent application is related to U.S. Provisional Application No. 62/763,166, filed Jun. 5, 2018, entitled "Disinfecting Opportunistic Premise Plumbing Pathogens Using Multiple Wavelength UV-LEDs" in the names of the Hodon Ryu and Hyoungmin Woo, which is incorporated herein by reference in its entirety. The present patent application claims the benefit under 35 U.S.C. § 119(e).

TECHNICAL FIELD

The present application relates generally to the technical field of water filters, and more specifically, to the technical field of a filter assembly for a water fixture for disinfecting pathogens from the water in the water fixture using ultraviolet (UV) Light Emitting Diodes (LEDs).

BACKGROUND

Water filters for attachment to a faucet, shower head or other plumbing fixtures have been around for many years. In general, these types of water filters may be inserted into a waterline prior to the water flowing to the plumbing fixture. The water filters take untreated water from a water line and discharges filtered water to the plumbing fixture.

Water filters that are inserted into the waterline prior to the plumbing fixture are generally designed to remove particulates from the water. These types of water filter may remove particles as small as 5 microns in size or smaller. However, these types of water filters generally have to be replaced on a routine basis. Further, these types of water filters are unable to remove chlorine or other oxidizing agents as well as different forms of bacteria and/or pathogens from the water.

There are water filters designed to remove chlorine or other oxidizing agents. Carbon filters have been designed for residential applications and may be used to remove chlorine from the water thereby improving water taste and odor. However, carbon filters have a relatively short life and by removing the chlorine or oxidizing agents, the treated water can become more susceptible to bacterial contamination. Further, carbon filters are unable to remove different forms of bacteria and/or pathogens from the water.

Further, present point-of-use (POU) filtration systems are unable to inactivate opportunistic premise plumbing pathogens (OPPPs) such as *Legionella*. *Legionella* bacteria can multiply in all kinds of water systems. The bacterium *Legionella pneumophila* is responsible for most cases of legionnaires' disease. Most people become infected when they inhale microscopic water droplets containing *Legionella* bacteria. This might be the spray from a shower, faucet or whirlpool, or water dispersed through the ventilation system.

Presently, to reduce the risk of *Legionella* bacteria growth in water systems, it is recommended that dead ends in pipe-work be removed, flush out infrequently used outlets, and clean and de-scale shower heads and hoses. However, presently there are no POU filtration devices that are capable of inactivating OPPPs such as *Legionella*.

Therefore, it would be desirable to provide a system and method that overcomes the above. The system and method would provide a POU filtration system that is able to inactivate OPPPs in hot water.

SUMMARY

In accordance with one embodiment, a point-of-use (POU) water filtration device is disclosed. The POU water filtration device has a container. A plurality of channels is formed within the container, water entering the container flowing through the plurality of channels. A plurality of Ultraviolet (UV) Light Emitting Diodes (LEDs) is provided. Each of the plurality of UV LEDs illuminates UV light down an associated channel of the plurality of channels.

In accordance with one embodiment, a point-of-use (POU) water filtration device is disclosed. The POU water filtration device has a container. A top cover is coupled to a top surface of the container enclosing the container. An opening is formed through the top cover allowing water to enter the container. A plurality of separations walls extends up from a floor of the container. The separation walls form a plurality of channels within an interior of the container, wherein each of the plurality of channels has at least one open end allowing water to flow through the plurality of channels. A plurality of Ultraviolet (UV) Light Emitting Diodes (LEDs) is attached to sidewalls forming a perimeter of the container. Each of the plurality of UV LEDs illuminates UV light down an associated channel of the plurality of channels. A lens is coupled to at least one of the UV LEDs. At least one drainage opening is formed in a floor of the container. The drainage opening allows the water entering the container to exit the container. A photo reactant material is coated on at least one of the floor, the top cover and the plurality of separations walls.

In accordance with one embodiment, a method for removing pathogens from a plumbing fixture is disclosed. The method comprises: constructing a plurality of flow channels within the plumbing fixture; coupling the plurality of flow channels together allowing water to flow from one of the plurality of channels to an adjacent channel of the plurality of channels; attaching at least one UV LED to illuminate UV light down an associated channel of the plurality of channels; and coating photo reactant material on at least one of the floor, the top cover and the plurality of separations walls, wherein dimensions of the plurality of flow channels are based on calculating effective UV irradiance doses to inactivate OPPPs.

BRIEF DESCRIPTION OF THE DRAWINGS

The present application is further detailed with respect to the following drawings. These figures are not intended to limit the scope of the present application but rather illustrate certain attributes thereof. The same reference numbers will be used throughout the drawings to refer to the same or like parts.

DESCRIPTION OF THE APPLICATION

Figure 1:
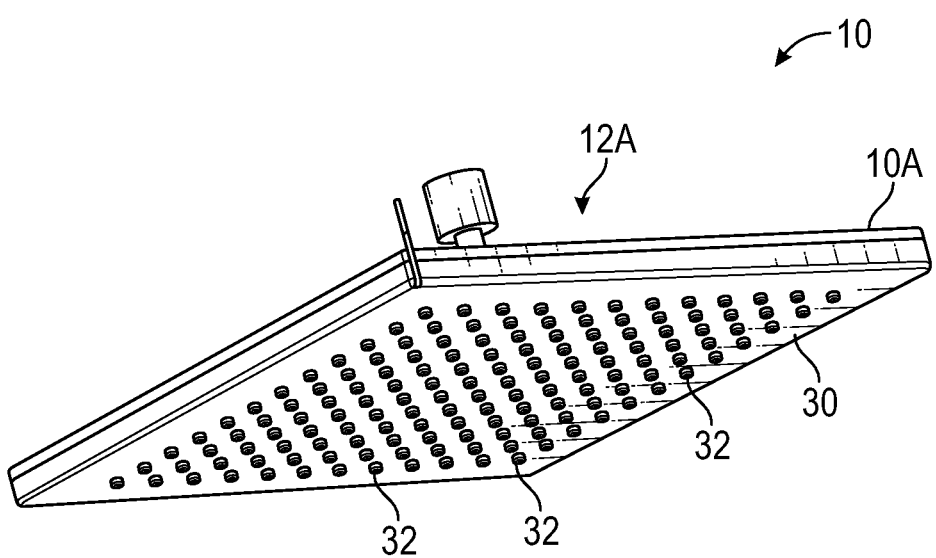
FIG. 1 is a bottom perspective view of an exemplary embodiment of a POU filtration device that is capable of inactivating OPPPs in accordance with one embodiment of the present invention.
Figure 2:
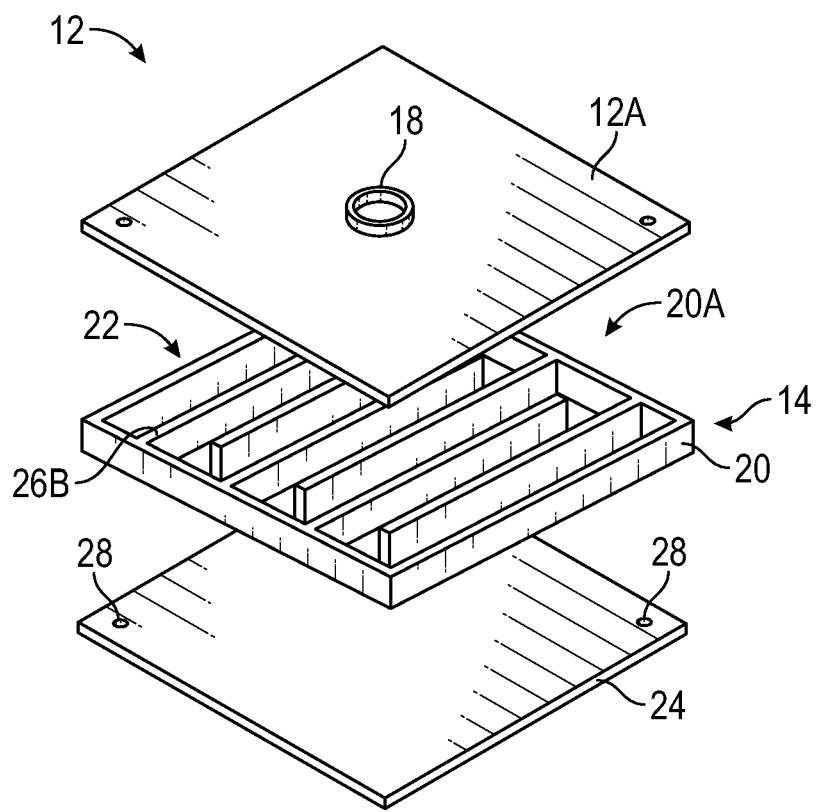
FIG. 2 is a partial exploded view of an exemplary embodiment of the POU filtration device of FIG. 1 in accordance with one embodiment of the present invention.
Figure 3:
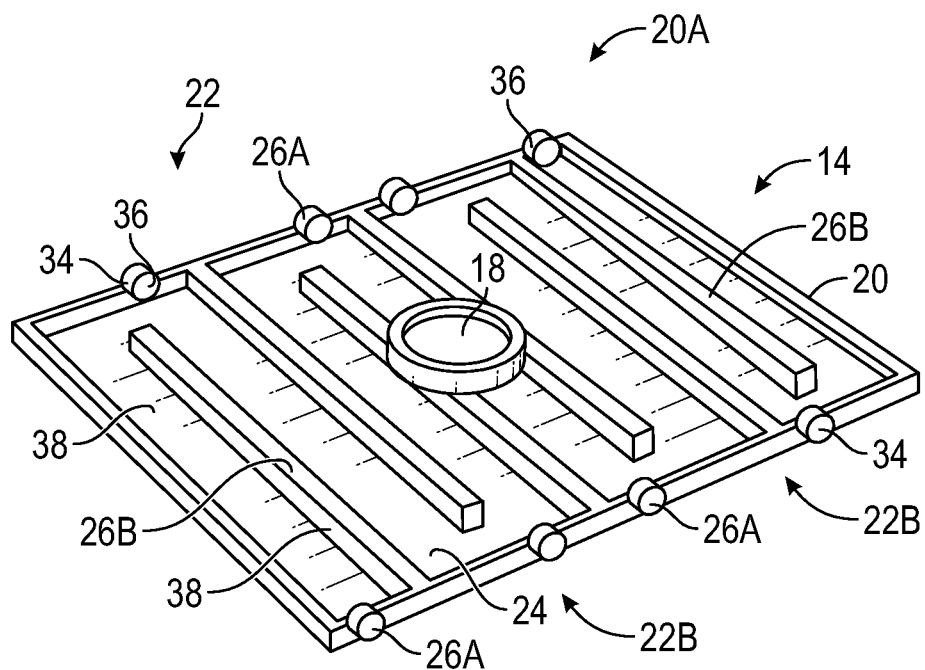
FIG. 3 is an elevated perspective view of an exemplary embodiment of the filtering unit of the POU filtration device of FIG. 1 in accordance with one embodiment of the present invention.
Figure 4:
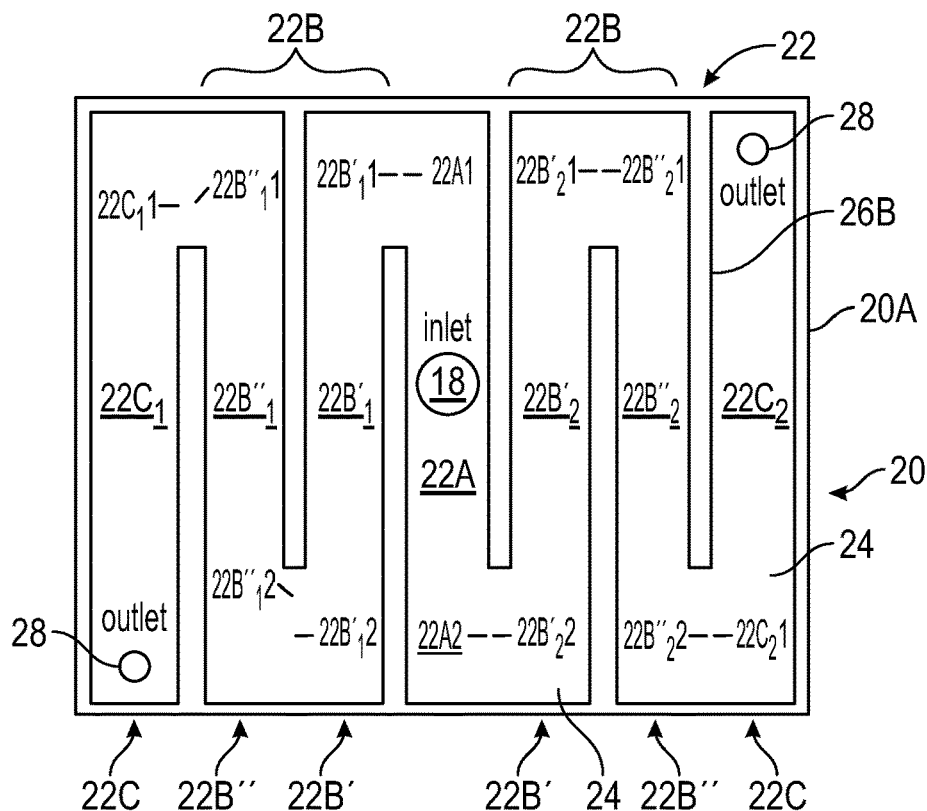
FIG. 4 is a top view of an exemplary embodiment of the filtering unit of the POU filtration device of FIG. 1 in accordance with one embodiment of the present invention.

The description set forth below in connection with the appended drawings is intended as a description of presently preferred embodiments of the disclosure and is not intended to represent the only forms in which the present disclosure can be constructed and/or utilized. The description sets forth the functions and the sequence of steps for constructing and operating the disclosure in connection with the illustrated embodiments. It is to be understood, however, that the same or equivalent functions and sequences can be accomplished by different embodiments that are also intended to be encompassed within the spirit and scope of this disclosure.

Embodiments of the exemplary system and method disclose a point-of-use (POU) filtration device that will inactivate opportunistic premise plumbing pathogens (OPPPs) such as *Legionella*. The system and method may utilize low power ultraviolet (UV) light emitting diodes (LEDs) positioned inside the POU filtration device. The low power UV LEDs may illuminate streams with multi-channel structures in order to inactivate OPPPs.

Referring to FIGS. 1-6, a point-of-use (POU) filtration device 10 may be seen. The POU filtration device 10 may be designed to inactivate opportunistic premise plumbing pathogens (OPPPs) such as *Legionella*. In the present embodiment, the POU filtration device 10 may be shown as a showerhead 10A. However, this is shown as one embodiment and should not be seen in a limiting manner. The POU filtration device 10 may be used with other plumbing fixtures without departing from the spirit and scope of the present invention.

The POU filtration device 10 may have a top cover 12, a filtering unit 14 and a bottom cover 16. The top cover 12 may be a planer member 12A. In the present embodiment, the top cover 12 may be square in shape. However, this is shown as one example and should not be seen in a limiting manner. The top cover 12 may be formed in other geometrical shapes based on the intended purpose or design. An opening 18 may be formed in a central area of the top cover 12. The opening 18 may be used to allow a waterline to be coupled to and supply the POU filtration device 10 with water.

The top cover 12 may be positioned on top of a filtering unit 14. The top cover 12 may be used to enclose the filtering unit 14 to prevent water from flowing out of a top area of the filtering unit 14. The filtering unit 14 may be formed of a container 20 having an open top surface 20A. The container 20 may be enclosed by coupling the top cover 12 over the open top surface 20A.

The filtering unit 14 may be designed to allow water entering through the opening 18 to flow through a plurality of channels 22 for water disinfection. The container 20 may have a plurality of channels 22 formed on a floor 24 of the container 20. The plurality of channels 22 may be formed by having a plurality of separation walls 26B attached to and extending up from the floor 24. In the present embodiment, the plurality of channels 22 run parallel to one another. Each channel 22 may be coupled to an adjacent channel 22 to allow water to flow through the filtering unit 14. In the present embodiment, each channel 22 may be coupled to an adjacent channel 22 to allow water to flow through the filtering unit 14 in a serpentine manner, i.e., up one channel 22 and down an adjacent channel 22 and/or vice versa.

In the present embodiment, the container 20 may have a center channel 22A. The center channel 22A may have an open end 22A1 and an open end 22A2. The open end 22A1 and the open end 22A2 may be formed on opposing ends of the center channel 22A and opposing sides. In the present embodiment, open end 22A1 may be formed on the upper end of the middle channel 22A and the open end 22A2 may be formed on the opposing end, the lower end of the center channel 22A. The open end 22A1 may be formed on a left side of the center channel 22A while open end 22A2 may be formed on the opposing side, the right side of the center channel 22A. However, this is shown as one embodiment and should not be seen in a limiting manner.

The filtering unit 14 may have one or more pair of side channels 22B. If pairs of side channels 22B are used, one side channel of each pair of side channels 22B may be positioned on each side (left side and right side) of the center channel 22A.

For example, in the present embodiment, a first pair of side channel 22B' may be provided. The first pair of side channel 22B' may be formed of side channels 22B'$_1$ and 22B'$_2$. Side channel 22B'$_1$ may be formed on the left side of and in fluid communication with the center channel 22A and the side channel 22B'$_2$ may be formed on the right side and in fluid communication with the center channel 22A.

Side channel 22B'$_1$ may have an open end 22B'$_1$1 and an open end 22B'$_1$2. The open end 22B'$_1$1 and the open end 22B'$_1$2 may be formed on opposing ends and opposing sides of the side channel 22B'$_1$. In the present embodiment, open end 22B'$_1$1 may be formed on the upper end of the side channel 22B'$_1$ and the open end 22B'$_1$2 may be formed on the opposing end, the lower end of the side channel 22B'$_1$. The open end 22B'$_1$1 may be formed on a right side of the side channel 22B'$_1$ and in fluid communication with the open end 22A1 of the center channel 22A. The open end 22B'$_1$2 of the side channel 22B'$_1$ may be formed on the opposing side, the left side of the side channel 22B'$_1$.

Side channel 22B'$_2$ may have an open end 22B'$_2$1 and an open end 22B'$_2$2. The open end 22B'$_2$1 and the open end 22B'$_2$2 may be formed on opposing ends and opposing sides of the side channel 22B'$_2$. In the present embodiment, open end 22B'$_2$1 may be formed on the upper end of the side channel 22B'$_2$ and the open end 22B'$_2$2 may be formed on the opposing end, the lower end of the side channel 22B"$_2$. The open end 22B'$_2$1 may be formed on a right side of the side channel 22B'$_2$. The open end 22B'$_2$2 of the side channel 22B'$_2$ may be formed on the opposing side, the left side of the side channel 22B'$_2$ and in fluid communication with the open end 22A2 of the center channel 22A.

In the present embodiment, the filtering unit 14 may have a second pair of side channel 22B". The second pair of side channel 22B" may be formed of side channels 22B"$_1$ and 22B"$_2$. Side channel 22B"$_1$ may be formed on the left side of the center channel 22A and in fluid communication with the side channel 22B'$_1$ of the first pair of side channels 22B' and the side channel 22B"$_2$ may be formed on the right side of the center channel 22A and in fluid communication with the side channel 22B'$_2$.

Side channel 22B"$_1$ may have an open end 22B"$_1$1 and an open end 22B"$_1$2. The open end 22B"$_1$1 and the open end $22B''_12$ may be formed on opposing ends and opposing sides of the side channel $22B''_1$. In the present embodiment, open end $22B''_11$ may be formed on the upper end of the side channel $22B''_1$ and the open end $22B''_12$ may be formed on the opposing end, the lower end of the side channel $22B''_1$. The open end $22B''_1$ may be formed on a left side of the side channel $22B''_1$. The open end $22B''_12$ of the side channel $22B''_1$ may be formed on the opposing side, the right side of the side channel $22B''_1$ and in fluid communication with the open end $22B'_12$ of the side channel $22B'_1$.

Side channel $22B''_2$ may have an open end $22B''_21$ and an open end $22B''_22$. The open end $22B''_21$ and the open end $22B''_22$ may be formed on opposing ends and opposing sides of the side channel $22B''_2$. In the present embodiment, open end $22B''_21$ may be formed on the upper end of the side channel $22B''_2$ and the open end $22B''_22$ may be formed on the opposing end, the lower end of the side channel $22B''_2$. The open $22B''_21$ may be formed on a left side of the side channel $22B''_2$ and in fluid communication with the open end $22B'_21$ of the side channel $22B'_2$. The open end $22B''_22$ of the side channel $22B''_2$ may be formed on the opposing side, the right side of the side channel $22B''_2$.

In the present embodiment, the filtering unit 14 may have a pair of end channels 22C. The pair of end channels 22C may be formed of end channel $22C_1$ and $22C_2$. End channel $22C_1$ may be formed on the left side of the center channel 22A and in fluid communication with the side channel $22B''_1$ of the second pair of side channels $22B_1$ and the end channel $22C_2$ may be formed on the right side of the center channel 22A and in fluid communication with the side channel $22B''_2$.

End channel $22C_1$ may have an open end $22C_11$. In the present embodiment, open end $22C_11$ may be formed on the upper end of the end channel $22C_1$. The open end $22C_11$ may be formed on a right side of the end channel $22C_1$ and in fluid communication with the open end $22B''_11$ of the side channel $22B''_1$.

End channel $22C_2$ may have an open end $22C_21$. In the present embodiment, open end $22C_21$ may be formed on the lower end of the end channel $22C_2$. The open end $22C_21$ may be formed on a left side of the end channel $22C_2$ and in fluid communication with the open end $22B''_22$ of the side channel $22B''_2$.

Located in each of the plurality of channels 22 is one or more Ultraviolet (UV) lights 26. The UV lights 26 may be used for UV disinfection of water flowing through the channels 22. In accordance with one embodiment, UV Light Emitting Diodes (LEDs) 26A may be used. The UV LEDs 26A will allow for lower power consumption than conventional mercury vapor lamps as well as to allow for a more compact design of the POU filtration device 10.

One or more UV LEDs 26A may be placed in each of the plurality of channels 22. In the present embodiment, the UV LEDs 26A may be placed either in an upper and/or lower end of each of the plurality of channels 22.

The UV LEDs 26A may be placed in a side wall 20A of the container 20. The side walls 20A may define an exterior perimeter of the container. The side walls 20A may provide a pathway for wiring for powering the UV LEDs 26A. Waterproof seals 34 may be used to prevent water from leaking into the side walls 20A.

Further, by placing the UV LEDs 26A either in an upper and/or lower section of each of the plurality of channels 22 and in the side wall 20A of the container 20, the UV LEDs 26A may emanate UV light down and through each of the plurality of channels 22 disinfecting the water as the water flows through the associated channel 22. A lens 36 or similar optical element may be attached to one or more to the UV LEDs 26A. The lens 36 may be used to focus and direct the UV light emanating from the UV LED 26A down and through each of the associated channel 22.

In the present embodiment, the UV LEDs 26A may be positioned at an end of each channel 22 where water may exit the associated channel 22. Thus, UV LEDs 26A may be placed at each end of the center channel 22A. The UV LEDs 26A may be located proximate each open end 22A1 and 22A2 of the center channel 22A. For side channel $22B'_1$, the UV LEDs 26A may be placed proximate the open end $22B'_12$. For side channel $22B'_2$, the UV LEDs 26A may be placed proximate the open end $22B'_21$. For side channel $22B''_1$, the UV LEDs 26A may be placed proximate the open end $22B''_11$. For side channel $22B''_2$, the UV LEDs 26A may be placed proximate the open end $22B''_22$. For the end channels $22C_1$ and $22C_2$, the UV LEDs 26A may be positioned near where water may exit the filtering unit 14. Thus, for the end channel $22C_1$, the UV LED 26A may be positioned near a lower end of the end channel $22C_1$. For the end channel $22C_2$, the UV LEDs 26A may be positioned near an upper end of the end channel $22C_2$.

To improve the efficacy of UV disinfection, the UV LEDs 26A may emit UV light in different frequencies. For example, different UV LEDs 26A may emit UV light in the UVA, UVB and/or UVC ranges. In accordance with the one embodiment, different UV LEDs 26A may emit UV light at 265 nm, 285 nm, and 380 nm. Thus, for example, the UV LEDs 26A in the center channel 22A may emit UV light at 285 nm, the UV LEDs 26A in the pairs of side channels 22B may emit UV light at 380 nm and the UV LEDs 26A in the pair of end channels 22C may emit UV light at 265 nm.

UV light in the 265 nm wavelength may be used as this wavelength is near the relative peak absorption of nucleic acids to target genomes of OPPPs. UV light in the 285 nm wavelength may be used as this wavelength is near the relative peak absorption of proteins to target protein-based regions of OPPPs. UV light in the 380 nm wavelength may be used to enhance advanced oxidation with photo-catalyst along with other UV LEDs as will be described below.

To improve the efficacy of UV disinfection, the top cover 12, the floor 24 and/or the separation walls 26B may be coated with photo reactant and/or UV reflective materials 38. In accordance with one embodiment, the top cover 12, the floor 24 and/or the separation walls 26B may be coated with a photo reactant material such as Titanium dioxide ($TiO_2$) and/or UV reflective materials such as aluminum foil and polytetrafluoroethylene (PTFE). The UV light from the UV LEDs 26A may cause a photocatalyst reaction which may generate oxidative species or hydroxyl radicals to inactivate pathogens. Titus, as described above, UV light in the 380 nm wavelength as well as the other wavelengths may be used to enhance advanced oxidation with the photocatalyst. The use of UV reflective materials may increase total UV irradiance exposure to flowing water and consequently enhance the inactivation efficacy of OPPPs in water.

The filtering unit 14 may have one or more drainage openings 28. The drainage openings 28 may be formed in the floor 24 of each end channel $22C_1$ and $22C_2$. The drainage openings 28 may allow water flowing through each end channel $22C_1$ and $22C_2$ to exit the filtering unit 14. In accordance with the present embodiment, the drainage openings 28 may be positioned in the end of each end channel $22C_1$ and $22C_2$ furthest from the open end $22C_11$ and open end $22C_21$ respectively.

Figure 5:
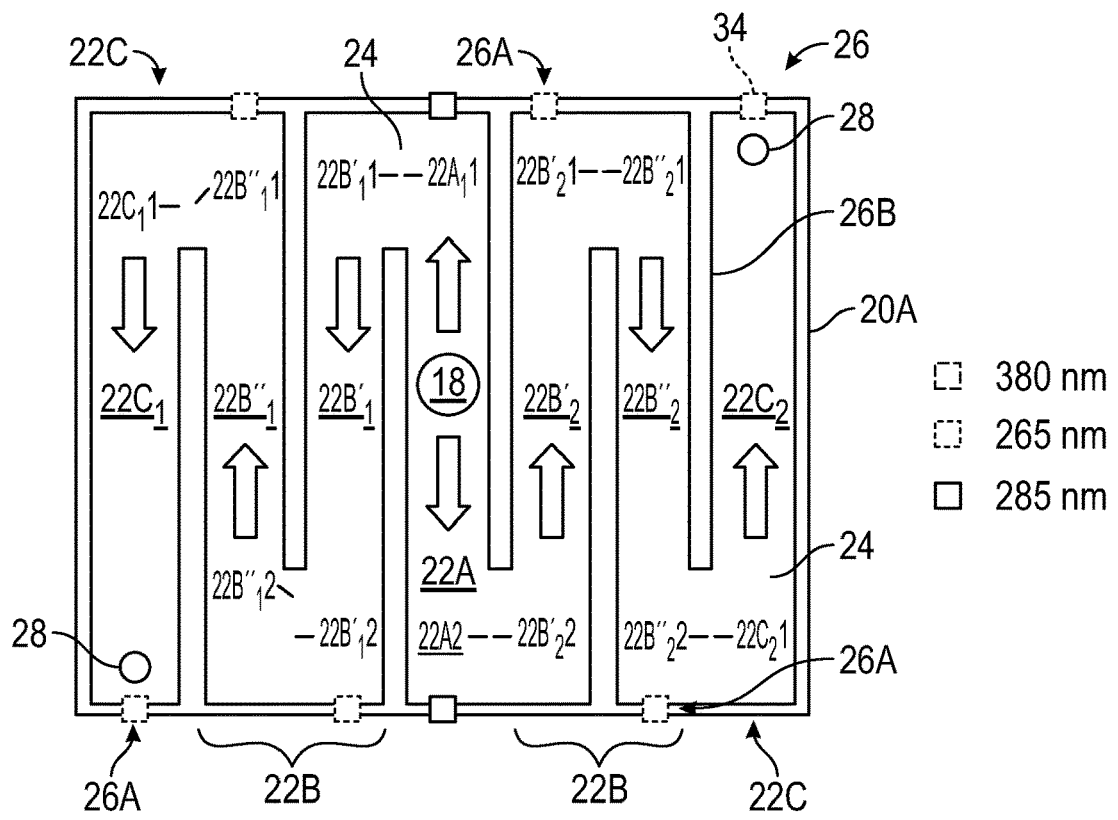
FIG. 5 is a top view of an exemplary embodiment of die filtering unit of the POU filtration device of FIG. 1 in accordance with one embodiment of the present invention.
Figure 6:
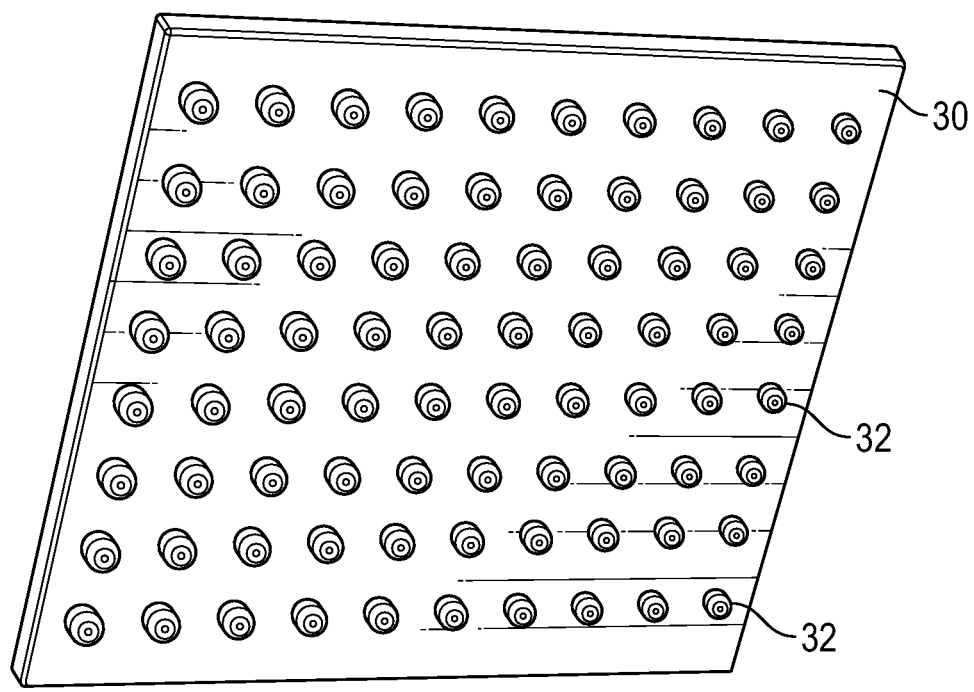
FIG. 6 is a bottom perspective view of an exemplary embodiment of the POU filtration device of FIG. 1 in accordance with one embodiment of the present invention.

As may be seen by the arrows in FIG. 5, water may enter the POU filtration device 10 through the opening 18 formed in the top cover 12. The opening 12 may be located above and in a middle area of the center channel 22A. The water entering the center channel 22A may flow out towards the open end 22A1 and the open end 22A2 where it may enter the first pair of side channel 22B'. The water may flow either into side channel $22B'_1$ or side channel $22B'_2$ via the open end $22B'_11$ or $22B'_22$ respectively. The water may flow through the side channel $22B'_1$ towards the open end $22B'_12$ and into the side channel $22B''_1$ via the open end $22B''_12$. Similarly, water may flow through the side channel $22B'_2$ towards the open end $22B'_21$ and into the side channel $22B''_2$ via the open end $22B''_21$. The water flowing through the side channel $22B''_1$ may flow out of the open end $22B''_11$ and into the end channel $22C_1$ via opening $22C_11$. Similarly, the water flowing through the side channel $22B''_2$ may flow out of the open end $22B''_22$ and into the end channel $22C_2$ via opening $22C_1$. Water flowing through the end channels $22C_1$ and $22C_2$ may then exit the filtering unit 14 via the drainage opening 28 located at the end of each end channel 22C. Once the water exits the filtering unit 14, the water will drain to a collection plate 30. The collection plate 30 may have one or more openings 32 to allow the water to exit the POU filtration device 10. In the present embodiment, the collection plate 30 may have a plurality of openings 32 formed in an array as the POU filtration device 10 may be used as a shower head. However, this is just one example as the POU filtration device 10 may be used with other plumbing fixtures.

The plurality of channels 22 may be configured to allow the UV LEDs 26A time to disinfect the water flowing therethrough. The dimension of the channels 22 may be based on the plumbing fixture the POU filtration device 10 is used with.

If the germicidal UV irradiation fluence energy reaches at above 1 mJ/cm$^2$ with effective UV dose and exposure duration, Legionella will be inactivated at 2-log scale (equivalent to 99% removal rate). The UV dose may be measured using a calibrated radiometer in units of milli-joules per square centimeter (mJ/cm$^2$) delivered by the UV disinfection device to the required level.

As an example, in one embodiment, the POU filtration device 10 may be used as a rain shower head. If the POU filtration device 10 has a configuration similar to that shown in FIGS. 1-6, the filtering unit 14 may be configured as having six separations walls 26B forming seven channels 22. For calculation purposes, each channel 22 may be 1 inch wide, 10 inches long, and ¼ inch in depth. The separation walls 26B may each be ½ inch in width. The water entering the opening 18 may be divided into two streams flowing in the opposite direction.

If a typical water shower uses 2.5 gallons per minute (gpm), then 1.25 gpm of water may flow in each direction through the channels 22. Thus, it takes about 2 seconds for water entering the opening 18 to flow out of one of the drainage openings 28. Each UV LED 26A may have at least 0.5 mW/cm$^2$ irradiance intensity to get 1 mJ/cm$^2$. For a typical shower head that supplies average flow rate at 2.5 gpm, the estimated water residence time is 1.82 sec (1.25 gpm=3.785*1.25=4.731 lpm, A=¼"*1"=0.25 inch$^2$=1.613 cm$^2$, V=Q/A=4.731 lpm/60 sec/min/1.613 cm$^2$*1000 cm$^3$/liter=48.884 cm/sec, flow path length for one channel=35"=88.9 cm, residence time=flow path/velocity=88.9 cm/48.884 cm/sec=1.82 sec).

For a reduced flow shower head that uses 30% less flow and supplies water with average flow rate at 2 gpm, the estimated water residence time is 2.27 sec (1 gpm=3.785 lpm, A=¼"*1"=0.25 inch$^2$=1.613 cm$^2$. V=Q/A=3.785 lpm/ 60 sec/min/1.613 cm$^2$*1000 cm$^3$/liter=39.109 cm/sec, flow path length for one channel=35"=88.9 cm, residence time=flow path/velocity=88.9 cm/39.109 cm/sec=2.27 sec).

The present invention provides a POU filtration device 10 that may inactivate OPPPs such as Legionella. The POU filtration device 10 may use low power UV LEDs 26A. The UV LEDs 26A may be positioned in a multi-channel structure in the POU filtration device 10. The UV light emitted by the UV LEDs 26A may inactivate OPPPs as water flows through the multi-channel structure in the POU filtration device 10. To improve the efficacy of UV disinfection, the UV LEDs 26A may emit UV light in different frequencies. For example, different UV LEDs 26A may emit UV light in the UVA, UVB and/or UVC ranges. The POU filtration device 10 may use a photo reactant and/or UV reflective material. The UV light from the UV LEDs 26A may cause a photocatalyst reaction which may generate oxidative species or hydroxyl radicals to inactivate microbial pathogens. Moreover, the use of UV reflective materials may increase total UV irradiance exposure to flowing water and consequently enhance the inactivation efficacy of OPPPs in water.

The foregoing description is illustrative of particular embodiments of the application but is not meant to be a limitation upon the practice thereof. The following claims, including all equivalents thereof, are intended to define the scope of the application.

What is claimed is:

1. A method for removing pathogens from a plumbing fixture comprising:
   constructing a plurality of flow channels within the plumbing fixture;
   coupling the plurality of flow channels together allowing water to flow from one of the plurality of channels to an adjacent channel of the plurality of channels;
   attaching at least one UV LED to illuminate UV light down an associated channel of the plurality of channels; and
   coating photo reactant material on at least one of a floor, a top cover and a plurality of separations walls of the plumbing fixture;
   wherein dimensions of the plurality of flow channels are based on calculating effective UV irradiance doses to inactivate opportunistic premise plumbing pathogens (OPPPs).

2. The method of claim 1, comprising injecting water into a center area of a center channel of the plurality of channels, wherein the water injected diverges and flows in opposing directions in the center channel.

3. The method of claim 1, comprising injecting water into a center area of a center channel of the plurality of channels, wherein the water injected diverges and flows in opposing directions in the center channel and out into adjacent channels of the plurality of channels.

4. The method of claim 1, comprising injecting water into a center area of a center channel of the plurality of channels so that the water injected diverges and flows in opposing directions in the center channel and out into adjacent channels of the plurality of channels in a serpentine manner.

5. The method of claim 3, comprising:
   collecting the water injected into the center channel and flowing through adjacent channels of the plurality of channels; and
   directing the collected water out of the plumbing fixture.

6. A method for removing pathogens from a plumbing fixture comprising:

forming a UV water filtration device within the plumbing fixture, wherein forming the UV water filtration device comprises:
constructing a plurality of flow channels within the plumbing fixture;
coupling the plurality of flow channels together allowing water to flow from one of the plurality of channels to an adjacent channel of the plurality of channels;
attaching at least one UV LED to illuminate UV light down an associated channel of the plurality of channels; and
coating photo reactant material on at least one of a floor, a top cover and a plurality of separations walls;
wherein dimensions of the plurality of flow channels are based on calculating effective UV irradiance doses to inactivate opportunistic premise plumbing pathogens (OPPPs).

7. The method of claim 6, comprising injecting water into a center area of a center channel of the plurality of channels, wherein the water injected diverges and flows in opposing directions in the center channel.

8. The method of claim 6, comprising injecting water into a center area of a center channel of the plurality of channels so that the water injected diverges and flows in opposing directions in the center channel and out into adjacent channels of the plurality of channels.

9. The method of claim 6, comprising injecting water into a center area of a center channel of the plurality of channels so that the water injected diverges and flows in opposing directions in the center channel and out into adjacent channels of the plurality of channels in a serpentine manner.

10. The method of claim 7, comprising:
collecting the water injected into the center channel and flowing through adjacent channels of the plurality of channels; and
directing the collected water out of the plumbing fixture.

11. A method for removing pathogens from a plumbing fixture comprising:
forming a UV water filtration device within the plumbing fixture, wherein forming the UV water filtration device comprises:
providing a container;
forming a plurality of channels within the container, each of the plurality of channels in fluid communication with an adjoining channel of the plurality of channels allowing water entering the container to flow through the plurality of channels, wherein forming the plurality of channels comprises:
forming a center channel, the center channel forming part of the plurality of channels, and having a pair of center channel open ends, the pair of center open ends formed on opposing ends of the center channel and on opposing sides of the center channel;
forming a pair of side channels, the pair of side channels forming part of the plurality of channels, wherein one of the pair of side channels is located on each side of the center channel and in fluid communication with the center channel; and
forming a pair of end channels, the pair of end channels forming part of the plurality of channels, wherein each one of the pair of end channels is in fluid communication with one of the pair of side channels;
attaching a top cover to a top surface of the container enclosing the container;
forming an opening in a central area of the top cover allowing the water to enter the container and into the center channel, wherein water entering flows into a center area of the center channel and flows in opposing directions in the center channel and in opposing serpentine manners through the center channel and through corresponding side channels and corresponding end channels; and
attaching at least one UV LED to illuminate UV light down each of the plurality of channels.

12. The method of claim 11, comprising: forming a pair of drainage openings in a floor of the container, the drainage openings allowing the water entering the container to exit the container, wherein one of the pair of drainage openings is formed in each of the pair of end channels and on opposing ends.

13. The method of claim 11, comprising:
attaching a collection plate to the container, wherein the collection plate is positioned below a floor of the container; and
forming a plurality of collection plate openings through the collection plate allowing the water to exit the container.

14. The method of claim 11, comprising applying at least one of a photo reactant or UV reflective materials on a floor of the container.

15. The method of claim 13, comprising applying at least one of photo reactant or UV reflective materials on a floor of the container and the top cover.

16. The method of claim 11, comprising applying at least one of photo reactant or UV reflective materials on separations walls forming the plurality of channels.

* * * * *